(12) United States Patent
McCloskey et al.

(10) Patent No.: US 9,699,391 B2
(45) Date of Patent: Jul. 4, 2017

(54) SYSTEMS AND METHODS FOR INFRARED DETECTION

(71) Applicant: RELEVANT PLAY, LLC, Boulder, CO (US)

(72) Inventors: David C. McCloskey, Erie, CO (US); Jeffrey L. Barnett, Fort Collins, CO (US); Stanley R. James, San Francisco, CA (US); John Robert Blakely, Niwot, CO (US); Bradley Matthew White, Lafayette, CO (US)

(73) Assignee: Relevant Play, LLC, Denver, CO (US)

( * ) Notice: Subject to any disclaimer, the term of this patent is extended or adjusted under 35 U.S.C. 154(b) by 266 days.

(21) Appl. No.: 14/300,791

(22) Filed: Jun. 10, 2014

(65) Prior Publication Data

US 2014/0362228 A1    Dec. 11, 2014

Related U.S. Application Data

(60) Provisional application No. 61/833,365, filed on Jun. 10, 2013, provisional application No. 61/902,524, filed on Nov. 11, 2013.

(51) Int. Cl.
*H04N 5/33* (2006.01)
*H04N 1/00* (2006.01)
(Continued)

(52) U.S. Cl.
CPC ............. *H04N 5/33* (2013.01); *A63F 13/213* (2014.09); *A63F 13/655* (2014.09); *A63F 13/69* (2014.09);
(Continued)

(58) Field of Classification Search
CPC ........ H04N 5/33; H04N 5/2256; H04N 5/332; H04N 1/00278; G01N 21/6456; G01N 2021/6417; G01N 2021/0221
(Continued)

(56) References Cited

U.S. PATENT DOCUMENTS 5,402,364 A    3/1995    Kitoh
5,691,909 A    11/1997    Frey et al.
(Continued)

FOREIGN PATENT DOCUMENTS

EP    1912059    4/2008
JP    2004-171109    6/2004
(Continued)

OTHER PUBLICATIONS

International Search Report with Written Opinion corresponding to International Patent Application No. PCT/US2014/041719, mailed Dec. 9, 2014.
(Continued)

*Primary Examiner* — Allen H Nguyen
(74) *Attorney, Agent, or Firm* — Lathrop & Gage LLP

(57) ABSTRACT

A fluorescence detection system includes a light source for coupling with a mobile device and software, having machine readable instructions loadable into memory of the mobile device and executable by a processor of the mobile device, capable of: activating the light source in coordination with capturing one or more images using a camera of the mobile device; analyzing an image captured with the light source on with an image captured with the light source off, to detect a shift of intensity within a predetermined color range within the images; and identifying and authenticating objects by measuring the intensity shift within the images.

8 Claims, 5 Drawing Sheets

(51) Int. Cl.
*H04N 5/225* (2006.01)
*A63F 13/655* (2014.01)
*A63F 13/213* (2014.01)
*A63F 13/69* (2014.01)
*G01N 21/64* (2006.01)
*G07D 7/12* (2016.01)

(52) U.S. Cl.
CPC ........... *G01N 21/6456* (2013.01); *G07D 7/12* (2013.01); *G07D 7/122* (2013.01); *H04N 5/2256* (2013.01); *H04N 5/332* (2013.01); *G01N 2021/6417* (2013.01); *G01N 2201/0221* (2013.01)

(58) Field of Classification Search
USPC .......................................................... 358/1.1
See application file for complete search history.

(56) References Cited

U.S. PATENT DOCUMENTS

| | | | |
|---|---|---|---|
| 5,971,276 A * | 10/1999 | Sano | G06K 7/12 235/462.01 |
| 6,512,993 B2 | 1/2003 | Kacyra et al. | |
| 6,612,494 B1 | 9/2003 | Outwater | |
| 7,599,732 B2 * | 10/2009 | Sevick-Muraca | A61B 5/0059 356/301 |
| 7,841,264 B2 | 11/2010 | Kim et al. | |
| 8,970,867 B2 * | 3/2015 | Baldwin | G06F 3/1238 358/1.1 |
| 2003/0112423 A1 | 6/2003 | Vig et al. | |
| 2004/0188528 A1 | 9/2004 | Alasia et al. | |
| 2008/0038494 A1 | 2/2008 | Midgley et al. | |
| 2011/0019914 A1 * | 1/2011 | Bimber | G02B 21/367 382/167 |
| 2011/0055053 A1 | 3/2011 | Rutschmann | |
| 2011/0075916 A1 | 3/2011 | Knothe et al. | |
| 2011/0117025 A1 | 5/2011 | Dacosta et al. | |
| 2012/0157160 A1 | 6/2012 | Ozcan et al. | |
| 2013/0135081 A1 | 5/2013 | McCloskey et al. | |
| 2013/0157351 A1 | 6/2013 | Ozcan et al. | |
| 2013/0215168 A1 * | 8/2013 | Furness, III | B41J 2/17546 347/6 |
| 2014/0034214 A1 * | 2/2014 | Boyer | B29C 67/0051 156/73.2 |
| 2014/0043630 A1 * | 2/2014 | Buser | H04N 13/02 358/1.13 |

FOREIGN PATENT DOCUMENTS

| | | |
|---|---|---|
| WO | 0124107 A2 | 4/2001 |
| WO | WO 02/061405 | 8/2002 |
| WO | WO 2013/003815 | 1/2013 |

OTHER PUBLICATIONS

PCT/US2012/067459 International Search Report & Written Opinion mailed Mar. 11, 2013; 10 pages.

MaxMax, Upconversion, Aug. 30, 2012, accessed on the Internet May 22, 2013, http://www.maxmax.com/alRUpConversion.asp; 3 pages.

MaxMax, IR Ink, Aug. 30, 2012, accessed on the Internet May 22, 2013, http://www.maxmax.com/aXRayIRInks.asp; 6 pages.

New Prismatic Co., Invisible Fluorescent Material, Sep. 6, 2010, accessed on the Internet May 22, 2013, http://www.colorchange.com.tw/english/index.php/invisible-fluorescent-introduction.html; 3 pages.

Supplemental European Search Report corresponding to European Patent Application No. 14810817.8, dated Dec. 15, 2016, 8 pages.

* cited by examiner

IR Color Layer Array on Cmos Sensor

SYSTEMS AND METHODS FOR INFRARED DETECTION

RELATED APPLICATIONS

This application claims priority to U.S. Patent Application Ser. No. 61/833,365, titled "Systems and Methods for Infrared Detection", filed Jun. 10, 2013, and incorporated herein by reference.

This application also claims priority to U.S. Patent Application Ser. No. 61/902,524, titled "Systems and Methods for Infrared Detection", filed Nov. 11, 2013, and incorporated herein by reference.

BACKGROUND

Many mobile phones and tablets include cameras designed to take pictures. These cameras typically use a CMOS (complementary metal-oxide semiconductor) sensor with an infrared cut-off filter designed to block near infrared photons from reaching the imaging sensor, while passing visible light. The IR cut-off filter prevents infrared radiation from distorting colors in images from colors as generally perceived by the human eye. While this results in more natural looking images, conventional mobile devices are unsuitable for detecting fluorescent emission at IR wavelengths without removal of the included infrared cut-off filter.

SUMMARY

In one embodiment, a fluorescence detection system includes a light source for coupling with a mobile device and software, having machine readable instructions loadable into memory of the mobile device and executable by a processor of the mobile device, capable of: activating the light source in coordination with capturing one or more images using a camera of the mobile device; analyzing an image captured with the light source on with an image captured with the light source off, to detect a shift of intensity within a predetermined color range within the images; and identifying and authenticating objects by measuring the intensity shift within the images.

In another embodiment, a fluorescence detection system includes software, having machine readable instructions loadable into memory of a mobile device and executable by a processor of the mobile device, capable of: activating a display of the mobile device to emit light in coordination with capturing one or more images using a camera of the mobile device; analyzing an image captured with the display on with an image captured with the display off, to detect a shift of intensity within a predetermined color range within the images; and identifying and authenticating an object by measuring the intensity shift within the images.

In another embodiment, a fluorescence detection system couples with a mobile device having a camera. The system includes a filter for placing over a flash of the camera, software, having machine readable instructions loadable into memory of the mobile device and executable by a processor of the mobile device, that is capable of: capturing a first image of an object using a camera of the mobile device when the flash is not active; activating the flash in coordination with capturing a second image of the object using the camera; analyzing the first and second images to detect a shift of intensity within a predetermined color range within the images based upon fluorescence from the object in response to activation of the flash; and identifying and authenticating the object based upon the detected shift in intensity.

In another embodiment, a near-IR filter array layer for an electromagnetic sensor array includes a plurality of infrared filters arranged over the sensor array such that, for each pixel of the sensor array, each infrared filter is configured to pass a different wavelength of electromagnetic radiation within the infrared wavelength band to one sensor of the pixel.

In another embodiment, a 3D printer has filament authentication, and includes a print engine for generating a 3D object using a filament of material, and an IR authenticator positioned to authenticate the filament before use by the print engine. Operation of the print engine is based upon authentication of the filament by the IR authenticator.

In another embodiment, a method authenticates a filament used in a 3D printer. An IR beam at a first wavelength is projected onto the filament within the 3D printer. IR fluorescence at a second wavelength from a dye within the filament is detected in response to the IR beam. The detected IR fluorescence indicates authentication of the filament within the 3D printer.

DETAILED DESCRIPTION

Figure 1:
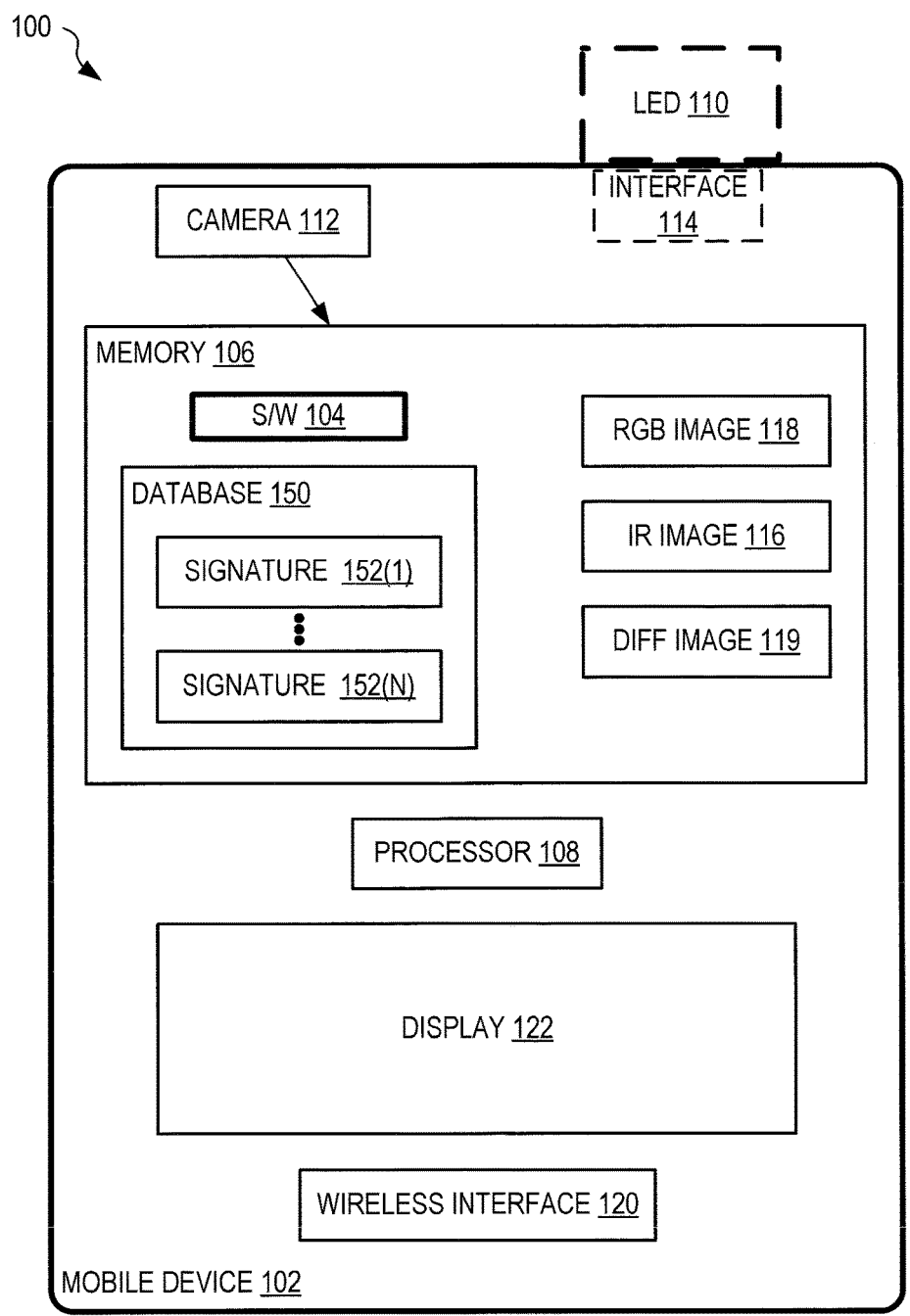
FIG. 1 schematically illustrates one exemplary fluorescence detection system coupled with a mobile device, illustrated as a smart phone, in an embodiment.

U.S. patent application Ser. No. 13/691,724, titled "System and Method for Authenticating Objects Using IR", filed Nov. 30, 2012, is incorporated herein by reference for enablement purposes.

Fluorescence Detection for Acquisition, Identity and Authentication within Visible Light Using the RGB Camera on Mobile Devices Disclosed is a solution for fluorescent detection using the camera of a mobile device. In particular, a system for fluorescent detection using a mobile device includes a light source such as an LED powered by the mobile device. The LED may be configured with the mobile device (e.g., a "flash" for use with the camera of the mobile device) or adapted for plugging into the mobile device (e.g., using the headphone jack of the mobile device). Software running on the mobile device activates the LED to illuminate an object/subject of interest in coordination with capturing one or more images of the object/subject using the on-board camera of the mobile device. A first image of the object, captured when the LED is turned off, is compared to a second image of the object, captured when the LED is turned on, by software to detect a shift of intensity for a given color range within the images. In one aspect, a blue to violet LED (e.g., 450 nm wavelength) is used to illuminate the object, and the software detects a shift of intensity within a red wavelength band when the object includes a material that fluoresces in the red wavelength band when excited by light at a wavelength of 450 nm. In another embodiment, a band-pass filter is applied to the LED "flash" of the mobile device such that when activated, the LED emits light of a particular wavelength.

The measured intensity shift allows the software on the mobile device to identify and authenticate objects. Identifying data may be hidden within the intensity shift, by combining known information about (a) the size of a fluorescent marker within or on the object that is used to gauge distance from the object with (b) the amount of intensity shift detected within the captured images.

For example, an object may be impregnated or coated (in part or in whole) with one or more fluorescent dyes. A fluorescent "signature" of the object may be measured using the LED and the camera as described above, and the information stored in memory accessible by the software. In one aspect, fluorescent signatures of a plurality of objects used in playing a mobile game may be included in gaming data stored within memory of the mobile device or accessible via the Internet.

When used in connection with a game, for example, the mobile device may be used to authenticate an action figure or other object, and thus, to "unlock" a corresponding character within the game. The mobile device may therefore replace USB platforms currently used to link toys/objects with video game characters, thus granting a player the freedom to play his or her game away from the platform.

In another aspect, software running on the mobile device controls an RGB LED to emit light within a desired wavelength band in coordination with image capture (i.e., to emit light of a desired color when taking a picture). For example, software controls the RGB LED to emit blue-violet light, in order to elicit a fluorescent response measurable in the red wavelength band. One or more images taken with the LED emitting in the desired wavelength band are processed with one or more images taken with the LED off, to determine an intensity shift in the red band, in order to identify and authenticate objects.

In another aspect, a filter may be placed over the flash of a mobile device camera, in order to limit emission by the flash, in order to elicit a measurable fluorescent response by the object. For example, a filter may block green and red emissions of the flash, to limit light striking the object to blue. An intensity shift within the red color channel may then be detected within captured images and analyzed to authenticate the object.

Dyes may be designed to regulate object emission. Given that the fluorescence is within visible light, the authentication process may be noticeable, barely noticeable, or hardly detectable to the human eye.

The disclosed systems and methods beneficially provide not only mobile authentication, but also rapid authentication. Mobile device cameras typically run at 24 to 30 frames per second, and as little as one frame is needed to capture a fluorescence response to an excitation wavelength in order to authenticate the object. Thus, noticeability by the human eye of the LED activation and of the corresponding fluorescence response would be negligible. However, additional frames may be used to provide data to sort against false positives.

A mobile device (such as an iPhone) may be configured with a fluorescence detection system for acquisition, identity and authentication of an object. An LED powered by the phone jack of the mobile device and attached with a back surface of the device, proximate the device camera and camera flash, emits at 450 nm. The object being detected is painted with a dye that fluoresces when illuminated by the LED, as shown in the image displayed on the mobile device screen. Note that the mobile device screen shows a standard, RGB image of the object as taken by the built-in mobile device camera, and an IR/differenced image in which object fluorescence is visible.

Figure 2:
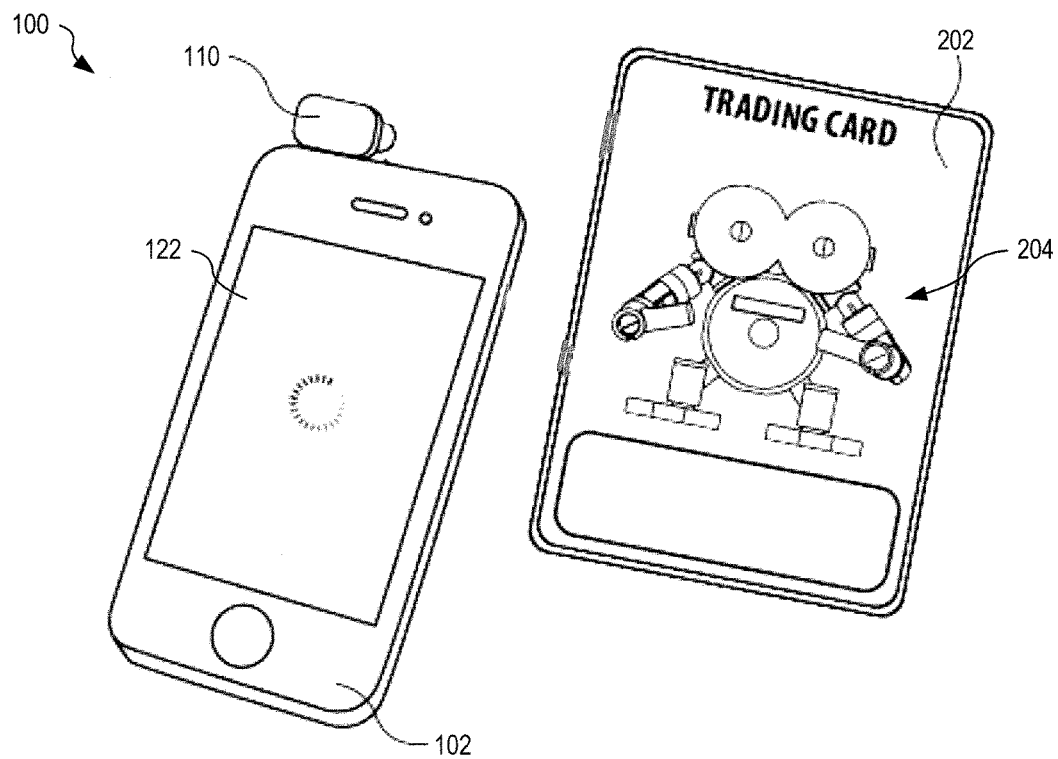
FIGS. 2 and 3 show a perspective view of operation of the mobile device of FIG. 1 to capture an IR image and an RGB image of an object to be authenticated.
Figure 3:
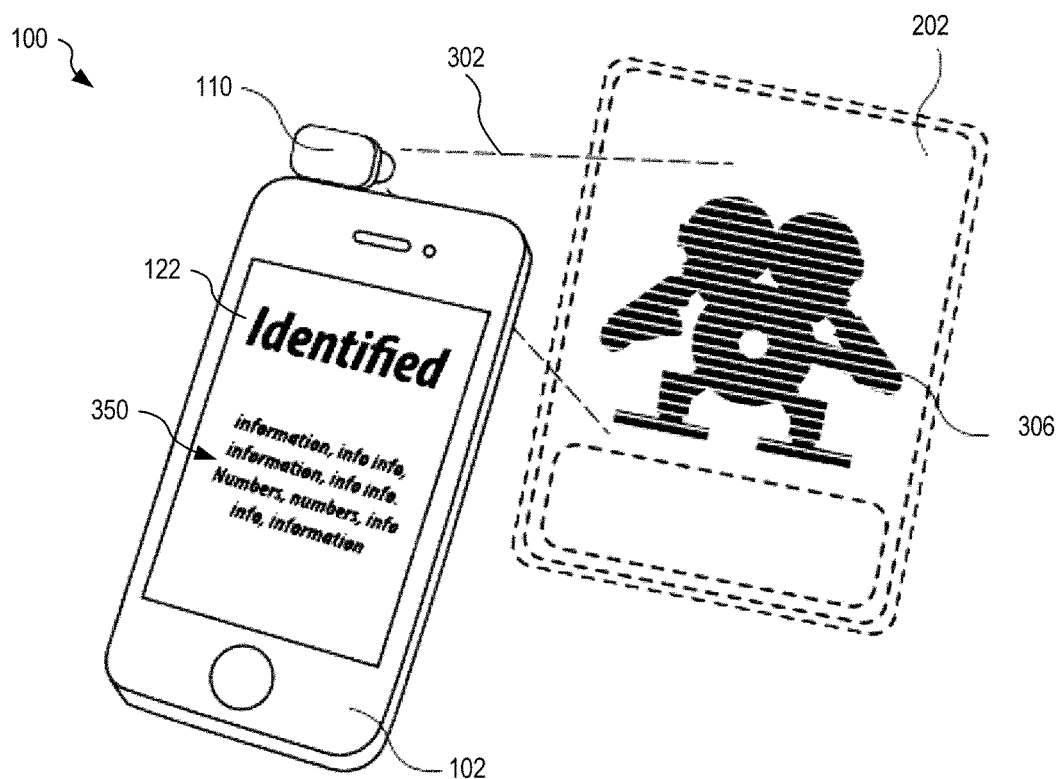
Figure 4:
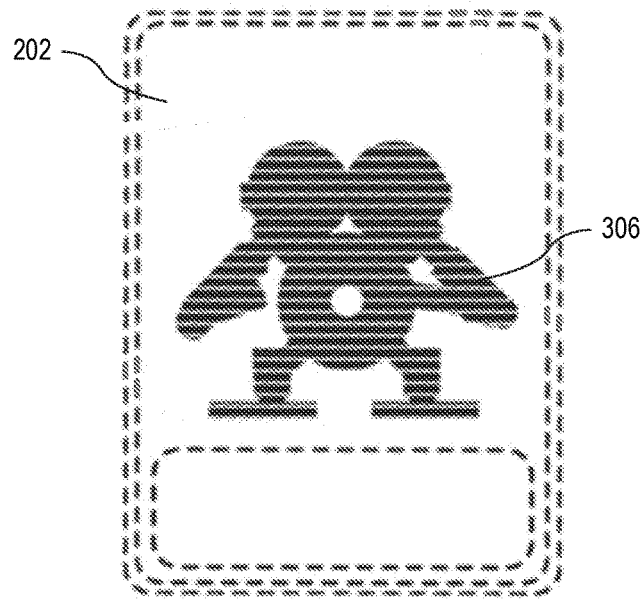
FIG. 4 shows exemplary location of the IR fluorescent dye within the object of FIG. 2.

FIG. 1 schematically illustrates one exemplary fluorescence detection system 100 configured as a mobile device 102, illustrated as a smart phone. FIGS. 2 and 3 show a perspective view of operation of mobile device 102 of FIG. 1 capturing an IR image 116 and an RGB image 118 of an object 202 to be authenticated. FIG. 4 shows exemplary location of IR fluorescent dye 306 within object 202. FIGS. 1, 2, 3 and 4 are best viewed together with the following description.

Software 104, stored within memory 106 of mobile device 102, includes machine readable instructions that when executed by a processor 108 of mobile device 102 interact with mobile device 102 to activate an LED 110 coupled with mobile device 102 in coordination with capturing one or more images of object 202 with a camera 112 of mobile device 102. LED 110 is for example powered by mobile device 102 at an interface 114, such as a jack of mobile device 102 for example. It will be appreciated that features of system 100 are placed as shown in FIG. 1 for purposes of illustration only, and that shown features (e.g., LED 110, interface 114, camera 112, a display 122 and others) may be located in positions other than those shown in FIG. 1.

At least one captured IR image 116 (captured by camera 112 when LED 110 is on), and at least one RGB image 118 (captured by camera 112 when LED 110 is off) are processed/compared by processor 108 to generate a difference image 119 for detecting a shift of intensity for a given color range within images 116 and 118. In one aspect, software 104 triggers LED 110 to flash in synch with a frame rate of camera 112 such that LED 110 is active to illuminate object 202 only during capture of alternate frames by camera 112. Software 104 then generates difference image 119 for pairs of captured images and may then evaluate color shifts of the red channel of camera 112 based upon red pixel values within IR image 116, RGB image 118, and difference image 119. In one embodiment, LED 110 represents a built-in "flash" LED of mobile device 102 that is controlled to provide illumination for use with camera 112.

In one example, where LED 110 emits light having a wavelength of 450 nm, software 104 detects a shift of intensity within a red wavelength band when the imaged object includes fluorescent dye 306 (or other material with fluorescing pigments) that fluoresces in the red wavelength band when excited by light at a wavelength of 450 nm. The measured intensity shift within the red wavelength band allows software 104 to identify and authenticate object 202 captured within images 116, 118.

Software 104, executed by processor 108, compares a measured intensity shift and other image data of images 116, 118, 119 with a database 150 of fluorescent signatures 152 of known, authentic objects to identity and authenticate an object within images 116, 118, where each signature 152 may define one or more of wavelength, position, shape, and other specifics of fluorescent marker(s) present within object 202. As shown, database 150 is stored in memory 106, but may be stored elsewhere that is otherwise accessible by software 104, for example from a database stored on a server and accessible via the Internet via a wireless interface 120.

IR Image 116, RGB image 118 and/or difference image 119 highlighting fluorescence of object 202 may be displayed on a display 122 of mobile device 102. As shown in FIG. 3, object identity/authentication and other information from database 150 may also be displayed on display 122, once object 202 is identified and authenticated. Upon identification and authentication, software 104 may trigger or invoke other actions, both on mobile device 102 and external thereto using wireless interface 120.

In one embodiment, display 122 is controlled by software 104 to display blue (e.g., to emit light at a 450 nm wavelength) to illuminate an object placed in front of display 122, thereby eliminating the need for LED 110. In this embodiment, camera 112 is forward facing on mobile device 102 to capture images of the object illuminated by light from display 112. Control (e.g., activation and deactivation) of display 122 is similar to control of LED 110 as described above, and camera 112 is controlled to capture RGB image 118 when display 122 is inactive, and to capture IR image 116 when display 1122 is emitting light at a 450 nm wavelength. This embodiment is particularly advantageous where mobile device 102 is a tablet computer that does not have a built in "flash" LED.

A Near-IR Filter Array Layer for CMOS Sensors

Most digital cameras made today, such as used in mobile communication devices, use a technology developed by Bryce Bayer of Eastman Kodak, a Bayer filter. The Bayer filter, or Bayer layer, is a "visible light" filter array comprised of red, green and blue color filters mounted directly before sensors grouped as pixels. Each filter of the array allows only photons of a specific color onto the corresponding sensor, where each pixel has one red, two green, and one blue filter and four corresponding sensors. Software then applies various demosaicing algorithms to determine color (e.g., a set of RGB values) for each pixel based upon sensed light levels and the geometry of the group of filters and sensors forming each pixel.

CMOS and CCD sensors are sensitive to light with wavelengths between about 400 and about 1100 nm, and therefore may be used to detect radiation in at least part of the near infrared (700-1200 nm) portion of the electromagnetic spectrum. However, since the Bayer layer allows only light within a human visible wavelength (e.g., 400 nm to 700 nm) to pass through, conventional cameras formed with the Bayer layer are unable to detect IR wavelengths and are not suited for infrared image capture. With the Bayer filters array removed, these conventional cameras detect only intensity levels of near IR radiation.

Figure 5:
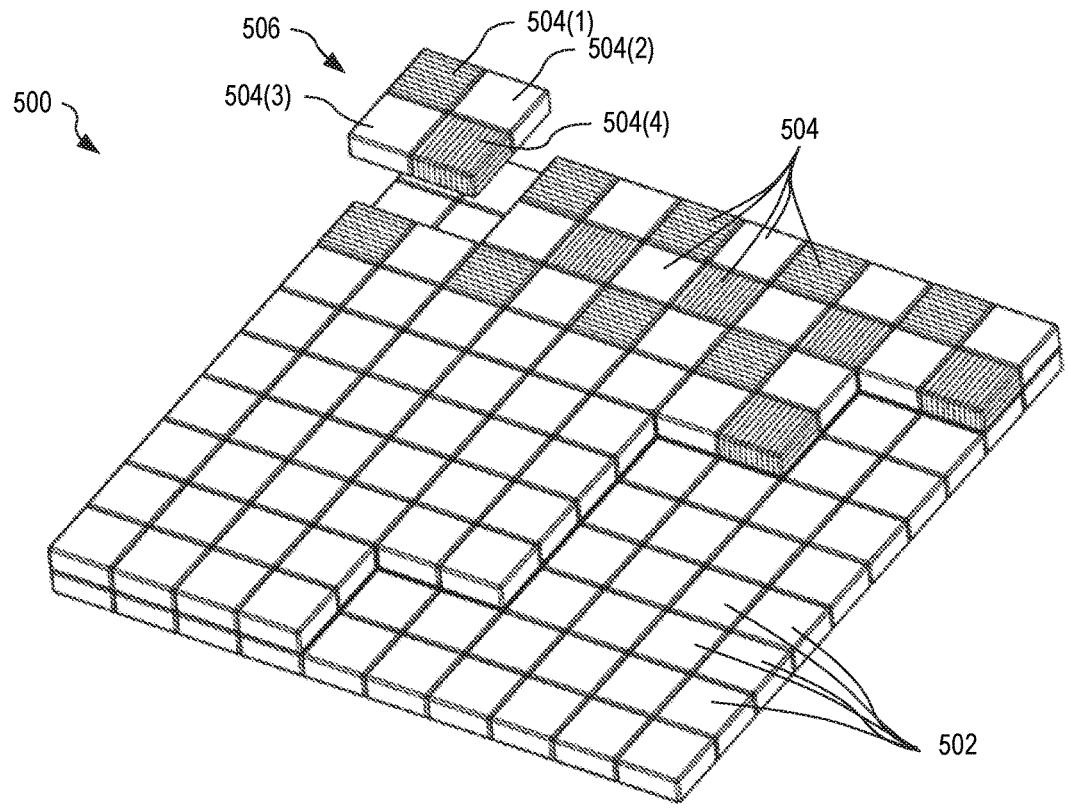
FIG. 5 is a schematic showing one exemplary IR image sensor for use in a digital camera, in an embodiment.
Figure 6:
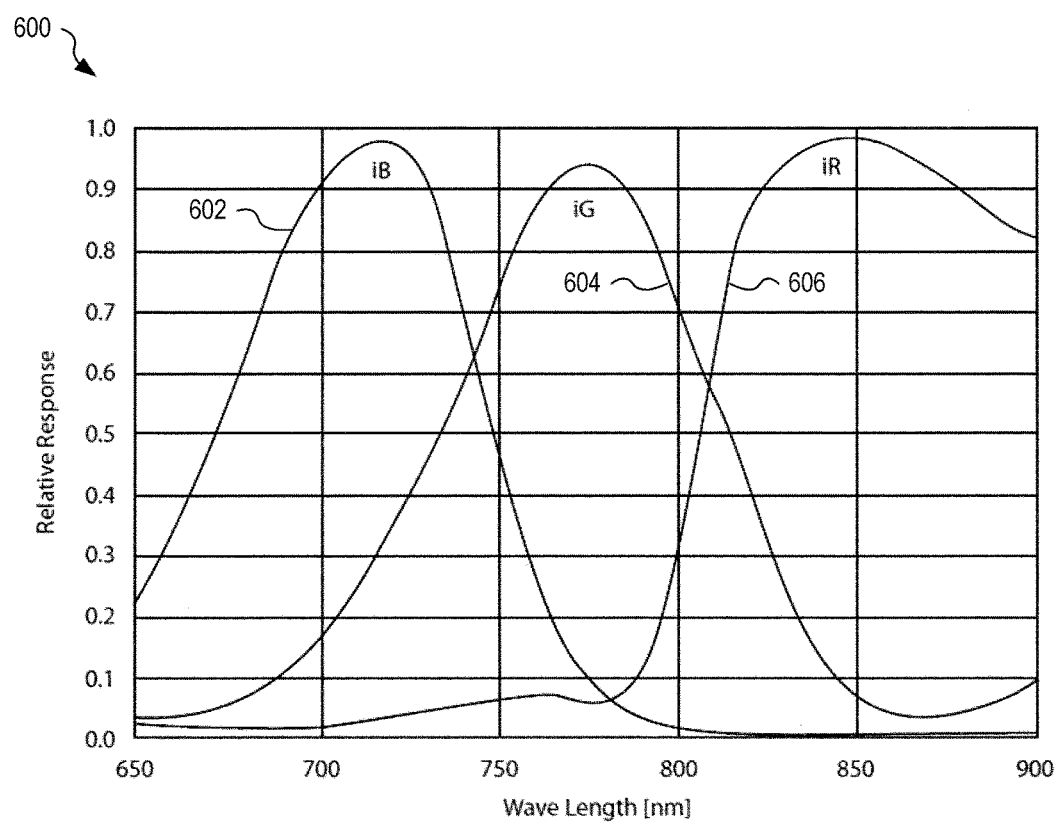
FIG. 6 is a graph showing three exemplary responses of the sensor and filter combinations of FIG. 5.

By replacing the Bayer layer with a filter array layer having portions that pass light in only certain bands of near infrared, the digital camera may be used to sense energy at specific infrared wavelengths. FIG. 5 is a schematic showing one exemplary IR image sensor 500 for use in a digital camera. IR image sensor 500 has an array of sensors 502 and an array of IR filters 504 positioned thereon. Sensors 502 and filters 504 are grouped into pixels 506 that each has four sensors 502 and four corresponding filters 504 in this example. Each sensor 502 operates to sense electromagnetic energy in the wavelength range of 700-1200 nm. Within each pixel 506, filters 504 are selected to pass IR energy at two or more different wavelengths. FIG. 6 is a graph showing three exemplary responses of sensor 502 and filter 504 combinations. In a first response 602, filter 504(1) has a pass band wavelength centered at 720 nm, in a second response 604, a filter 504(2) has a pass band wavelength centered at 775 nm, and in a third response 606, a filter 504(3) has a pass band wavelength centered at 845 nm. As appreciated, where additional sensitivity is desired, two or more filters 504 may be configured at the same pass band wavelength. Further, pixels may have more than four sensors 502 and filters 504 such that greater selectivity within the near IR waveband may be achieved. In one embodiment, within each pixel 506, certain filters 504 are selected to pass visible light (e.g., as with conventional Bayer filters) and other filters are configured to pass only IR wavelengths as shown in FIG. 6, wherein software (e.g., software 104) operates to selectively process output for sensors 502 for each pixel 506 to generate one or both of a visible image and an IR image. Where specific wavelengths are configured within filters 504, the software may operate to identify specific frequency responses from object 202 for purposes of authentication. For example, an object may be configured with multiple fluorescing dyes that fluoresce at different wavelengths, where filters 504 are configured to determine presence or absence of these fluorescent responses to achieve stronger authentication.

In one embodiment, camera 112 of system 100 is configured with image sensor 500 of FIG. 5 and used for infrared photography, detection and authentication. As described above, LED 110 is controlled by software 104 to elicit a fluorescent emission from object 202 tagged (impregnated or otherwise marked) with fluorescent dye 306. For example, software 104 activates LED 110 to illuminate object 202 in coordination with capturing IR image 116, deactivates LED 110 in coordination with capturing RGB image 118, where RGB image 118 does not represent a visible image, but is used to detect background IR levels. Software 104 then compares IR image 116 with RGB image 118 to generate difference image 119 that has background levels of IR removed. Software 104 may then process selective sensors 502 values for each pixel 506 within difference image 118 to identify a fluorescent response "signature" (a fluorescent stamp, pattern, marking, complex emission or simple emission) of object 202. Additional multiple wavelength analysis of IR image 116 and/or difference image 119 may be performed to determine object identity and authentication, for example by comparing a unique spectral signature of the dye or material (or combinations thereof) with a database of signatures of tagged objects.

Dye in Filament for 3D Printing

Used in cooperation with fluorescent detection, companies may digitally distribute their physical goods, by adding one or more IR fluorescing dyes of a known frequency response to filament, fibers or resins used to manufacture items through 3D printing. The filament/resin/fiber (which may be used interchangeably hereafter) may be impregnated with or produced with one or more dyes that fluoresce at a known wavelength when illuminated by a light source.

Figure 7:
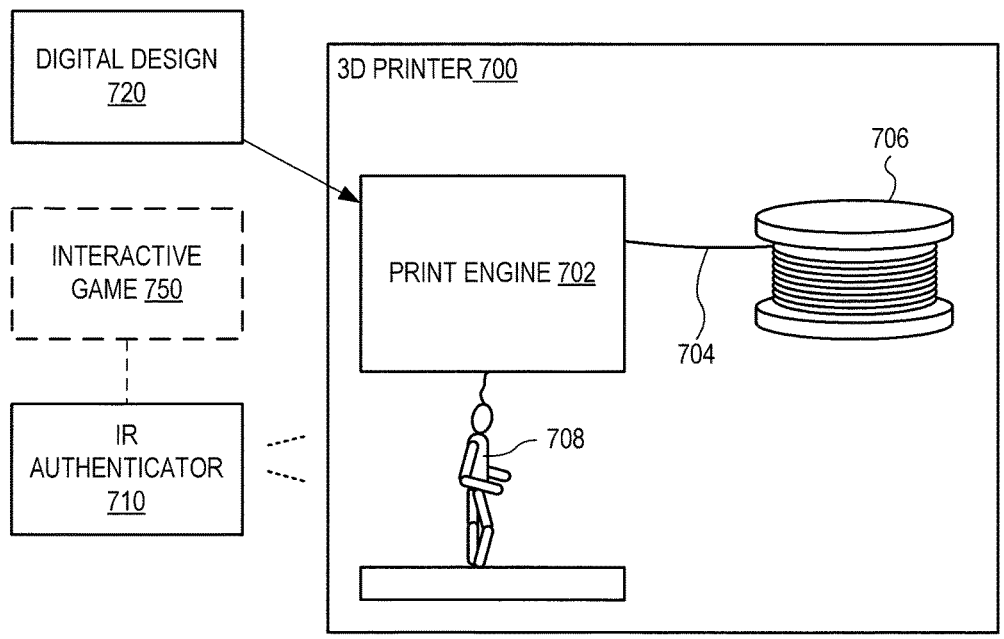
FIG. 7 shows one exemplary 3D printer for printing a 3D object that may be externally authenticated, in an embodiment.

FIG. 7 shows one exemplary 3D printer 700 for printing a 3D object 708 that may be externally authenticated. 3D printer 700 includes a print engine 702 that uses a filament consumable 704 such as a resin, illustratively shown supplied on a reel 706, for creating 3D object 708. A consumer purchases filament consumable 704 and downloads a digital design 720 for printing 3D object 708 from the resin. The consumer may then print (create) 3D object 708 using 3D printer 700. By purchasing and using resin 704 to create 3D object 708, 3D object 708 may be used interactively with other devices. For example, as shown in FIG. 7, an IR authenticator 710 (e.g., system 100 of FIG. 1) is used to (a) authenticate 3D object 708 based upon pigments within resin 704 from which 3D object 708 has been made, and (b) provide input to an interactive game 750. Without authentication of 3D object 708, interactive game 750 may have reduced or no functionality. Thus, to use 3D object 708 for participation with interactive game 750, the consumer is required to purchase and use resin 704 within 3D printer 700 when creating 3D object 708.

For example, IR authenticator 710 may include a computer/microprocessor, an IR projector, and an IR camera, and optionally an RGB camera. 3D object 708 is detected within a field of view of the IR camera (and optional RGB camera). Images of the object are captured with the camera, with the IR projector turned off and with the IR projector turned on, and the images are processed to detect a fluorescent response of the dye incorporated with 3D object 708. A fluorescent signature of 3D object 708 may be authenticated via an authentication algorithm, thus allowing 3D object 708 become interactive with game 750. In another example, authentication of 3D object 708 by IR authenticator 710 may unlock promotions offered via an external system for identifying specific objects (for example, a team jersey worn at a sporting event or while viewing a sporting event in front of a Smart TV).

In another example, 3D object 708 represents a building block or other component of a children's toy, that is then identified and authenticated by IR authenticator 710 to unlock functionality of a third party system or device looking for the authenticated 3D object 708.

This technology may lower the cost of manufactured goods, as authentic products may be created at home or at local stores or distribution centers. In addition, new revenue streams may grow from consumers licensing and downloading digital files needed to print desired objects from the tagged filament/resin/fiber (e.g., filament/resin/fiber 704). Furthermore, objects made with tagged resin may be authenticated and the owner of the objects may receive a warranty for authenticated objects.

In another example of use, where filament 704 is used to print potentially dangerous objects, such as plastic weapons, filament 704 may be may be tagged with an invisible IR dye or combination of dyes that fluoresce at known wavelengths, such that a printed weapon may be detected by systems for detecting IR response incorporated into airport security for example.

3D Printer Consumable Authentication

Figure 8:
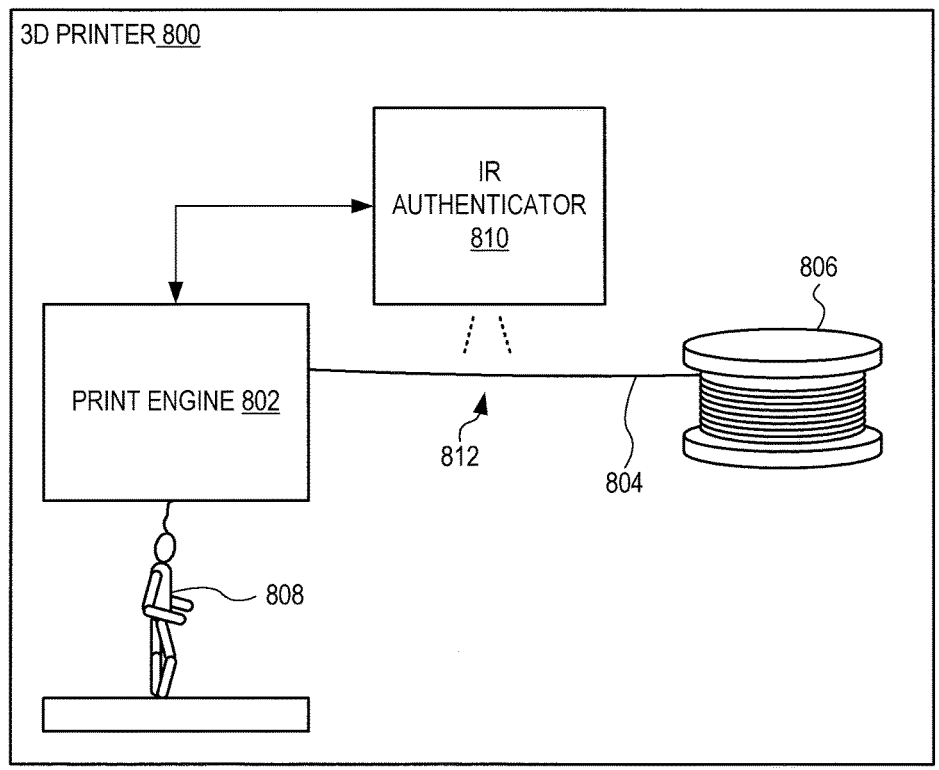
FIG. 8 shows one exemplary 3D printer with 3D printer consumable authentication, in an embodiment.

FIG. 8 shows one exemplary 3D printer 800 with 3D printer consumable authentication, in an embodiment. 3D printer 800 includes a print engine 802 that uses a filament consumable 804, illustratively shown supplied on a reel 806, for creating a 3D object 808. Print engine 802 is coupled with an IR authenticator 810 that is invoked to authenticate filament 804. IR authenticator 810 includes an IR source and an IR detector (e.g., a camera capable of detecting IR wavelengths) that cooperate to detect presence of IR fluorescing pigments (e.g., dyes) within filament 804 in the beam of the IR source, for example at location 812. In one embodiment, IR authenticator 810 utilizes simple, low-cost and commonly available sensors (e.g., photodiode, phototransistors, CMOS and/or other sensors) for detection of fluorescence from dyes within filament 804.

In one embodiment, location 812 is within 3D printer 800 and positioned on a path of filament 804 as it is taken from reel 806 into print engine 802. In another embodiment, IR authenticator 810 detects fluorescence of pigments within filament 804 while it is still on reel 806.

In one example of operation, print engine 802 controls IR authenticator 810 to authenticate filament 804 when installed into 3D printer 800, wherein IR authenticator 810 generates IR at a first wavelength, and detects corresponding IR fluorescence at a second wavelength from one or more IR fluorescing dyes present within filament 804. In one embodiment, first and second wavelengths are 30-80 nm or more apart, for example.

In one embodiment, print engine 802 utilizes identification of IR fluorescence to configure operating parameters for using filament 804. For example, presence or absence of one or more of a plurality of fluorescence responses may be used to specify processing parameters (e.g., temperature, feed rate, heat bed temperature, etc.) for using filament 804, wherein print engine 802 is thereby configured automatically when filament 804 is changed and a new IR "signature" identified.

In another embodiment, functionality of print engine 802 is restricted when filament 804 is not authenticated by IR authenticator 810. For example, 3D printer 800 may not function if filament 804 is not authenticated by print engine 802. A product manufacturer may release a 3D print design file of an object 808 that is associated with filament 804, wherein 3D printer 800 does not print the 3D print design unless the specific filament 804 is authenticated. The product manufacturer, or a third party associated with the manufacturer, may sell filament 804 at a premium price for use with 3D printer 800 to print one or more copies of the object from the 3D design file. In this example, printer 800 compares a fluorescence response of filament loaded into the printer with the fluorescence response expected of authentic filament 804 from the manufacturer. If the fluorescence responses do not match, print engine 802 inhibits generation of object 808. That is, unless IR authenticator 810 authenticates filament 804 within 3D printer 800, object 808 will not be printed. In one example, printer 800 will not run or complete the 3D design file if the filament is not authentic filament 804. In another example, print engine 802 is locked if authentication fails. A fluorescent signature of the filament may be authenticated via an authentication algorithm run by IR authenticator 810.

In one embodiment, print engine 802 and IR authenticator 810 may periodically authenticate filament 804 during printing of object 808, wherein failure to authenticate filament 804 may interrupt generation of object 808.

In another embodiment, print engine 802 is configured based upon identification and authentication of filament 804 by IR authenticator 810. For example, output quality of print engine 802 may be determined based upon authentication of filament 804, where the quality of material of filament 804, as identified and authenticated by IR authenticator 810, defines the output quality of print engine 802.

By authenticating filament 804 by IR authenticator 810 within 3D printer 800 and restricting functionality of print engine 802 based upon authentication, a printer manufacturer may direct users of 3D printer 800 to use a particular filament 804, such as from a preferred supplier. For example, a third party filament supplier would not include fluorescing dyes within the filament, or would not include the unique fluorescent signature of the particular filament 804, and thereby this third party product could not be used within 3D printer 800, or could be used only with reduced performance of 3D printer 800.

Although the example embodiments herein utilize an IR band for fluorescence, other bands may be used without departing from the scope hereof.

Fluorescing dyes may be added to other 3D printer filament materials, such as one or more of rubbers, metals, gelatins/lipids (e.g., for printing artificial tissues), stainless steel, brass, wood pulp-plastic mixtures, nylon, polyester, graphene/carbon fiber, ceramic, bacteria, and paper.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A 3D printer with filament authentication, comprising:
 a print engine for generating a 3D object using a filament of material; and
 an infrared (IR) authenticator positioned to authenticate the filament before use by the print engine the IR authenticator comprising:
  an IR generator for generating IR at a first wavelength; and
  an IR detector for detecting fluorescence of a dye within the filament at a second IR wavelength;
  wherein the authentication of the filament is based upon detection of the fluorescence at the second IR wavelength;
 wherein operation of the print engine is based upon authentication of the filament by the IR authenticator.

2. The 3D printer of claim 1, wherein the print engine initiates authentication of the filament when the filament is installed into the 3D printer.

3. The 3D printer of claim 1, wherein the print engine initiates authentication of the filament periodically during operation of the print engine.

4. The 3D printer of claim 1, wherein configuration of the print engine is based at least in part upon the authentication of the filament.

5. The 3D printer of claim 1, wherein at least one parameter of the print engine is configured based upon the detected florescent response of the dyes within the filament.

6. The 3D printer of claim 1, wherein the detected fluorescent response of the dyes identifies a type of the filament.

7. A method for authenticating a filament used in a 3D printer, comprising:
 projecting, within the 3D printer, an IR beam at a first wavelength onto the filament; and
 detecting, in response to the IR beam, IR fluorescence at a second wavelength from a dye within the filament;
 wherein the detected IR fluorescence indicates authentication of the filament within the 3D printer.

8. The method of claim 7, wherein the steps of projecting and detecting are repeated periodically during operation of the 3D printer.

* * * * *